United States Patent [19]

Schocket

[11] Patent Number: 4,722,724
[45] Date of Patent: Feb. 2, 1988

[54] ANTERIOR CHAMBER TUBE SHUNT TO AN ENCIRCLING BAND, AND RELATED SURGICAL PROCEDURE

[76] Inventor: Stanley Schocket, 3509 Anton Farms Rd., Baltimore, Md. 21208

[21] Appl. No.: 877,342

[22] Filed: Jun. 23, 1986

[51] Int. Cl.⁴ .......................................... A61M 27/00
[52] U.S. Cl. ......................................... 604/8; 604/294
[58] Field of Search ..................................... 604/8–10, 604/265, 266, 294

[56] References Cited

U.S. PATENT DOCUMENTS

| | | | |
|---|---|---|---|
| 3,736,939 | 6/1973 | Taylor | 604/265 |
| 3,788,327 | 1/1974 | Donowitz et al. | 128/350 R |
| 3,976,081 | 8/1976 | Lapidot | 604/265 |
| 4,249,535 | 2/1981 | Nargest | 604/265 X |
| 4,402,681 | 9/1983 | Haas et al. | 604/9 |
| 4,457,757 | 7/1984 | Molteno | 604/294 |
| 4,554,918 | 11/1985 | White | 604/10 |
| 4,640,087 | 8/1986 | Joseph | 604/9 |

OTHER PUBLICATIONS

Hufnagel et al., Surgery, vol. 61, No. 1, pp. 11–16, Jan. 1967.
Molteno et al, "Two-Stage Insertion of Glaucoma Drainage Implants", *Trans Opthal. Soc. N.Z.*, 31, pp. 17–26, 1979.
White, "A New Implantable Ocular Pressure Relief Device: A Preliminary Report", *Glaucoma*, 7, pp. 289–294, 1985.
Schocket et al, "Anterior Chamber Tube Shunt to an Encircling Band in the Treatment of Neovascular Glaucoma", *Opthalmology*, 89, pp. 1188–1194, 1982.
Schocket et al, "Anterior Chamber Tube Shunt to an Encircling Band in the Treatament of Neovascular Glaucoma and Other Refractory Glaucomas", *Opthalmology*, 92, pp. 553–562, 1985.
Krupin et al, "Valve Implants in Filtering Surgery", *American Journal of Opthalmology*, vol. 81, pp. 232–235, 1976.

Primary Examiner—Dalton L. Truluck
Attorney, Agent, or Firm—Fleit, Jacobson, Cohn & Price

[57] ABSTRACT

An implant and a surgical technique involving the anterior chamber tube shunt to an encircling band treatment for reducing neovascular and other refractory glaucomas is disclosed. The implant includes two connected tubes or a tube connected to a band, one tube being located in the anterior chamber of the eye and the second tube or the band being located around the orbit of the eye. A destructible valve is located in the tube in the region of the anterior chamber to temporarily restrict flow of aqueous and thereby prevent hypotony. Additionally, the implant may be treated with a heparin complex before implantation of the device. In the embodiment of the invention utilizing two tubes, one is larger than the other and has 50 micron holes through its wall to aid in diffusion of aqueous from the anterior chamber into the orbit.

13 Claims, 8 Drawing Figures

ANTERIOR CHAMBER TUBE SHUNT TO AN ENCIRCLING BAND, AND RELATED SURGICAL PROCEDURE

BACKGROUND OF THE INVENTION

1. Field of the Invention

The present invention relates to an implant and a surgical technique for treating neovascular glaucoma, and particularly to improvements in the anterior chamber tube shunt to an encircling band procedure.

2. Description of Prior Art

Glaucoma, a disease of the eye which may ultimately cause blindness, is caused by increased intraocular pressure. Since as early as 1906, surgical techniques have been attempted to treat glaucoma by lowering intraocular pressure. A modern surgical technique has been described by Schocket et al, in an article entitled "Anterior Chamber Tube Shunt to an Encircling Band in the Treatment of Neovascular Glaucoma", *Ophthalmology*, Vol. 89, No. 10, pp. 1188–1194, 1982, and in another article entitled "Anterior Chamber Tube Shunt to an Encircling Band in the Treatment of Neovascular Glaucoma and other Refractory Glaucomas", *Ophthalmology*, Vol. 92, No. 4, pp. 553–562, 1985.

According to the teachings of the above mentioned articles, aqueous is shunted from the anterior chamber of the eye to the orbit in order to reduce the intraocular pressure. The aqueous escapes through a tube inserted into the anterior chamber which is connected to a band which encircles the circumference of the eye. The aqueous fluid is shunted to an encapsulated reservoir and then diffuses through the capsular wall into the orbit to thereby lower the intraocular pressure.

Approximately two weeks after such surgery, the implanted materials become surrounded by a fibrous capsule separating the implant from the host tissue, a capsule that is contiguous with the tissue but not adherent to the implant. The capsule is apparently an attempt to destroy or isolate what the host tissue recognizes to be a foreign body. This encapsulation is essential for success and recovery in response to the surgical procedure.

Although this above-described work was a significant advance over the art, the implant of this surgical procedure can be improved. First, the surgically treated eye could be subject to bleeding into the anterior chamber. This could potentially occur at the time of insertion of the tube into the anterior chamber or shortly thereafter. As a consequence, blood clotting could occur which could block the opening in the tube needed to transport the aqueous from the eye, cause an increase in intraocular pressure, and render the procedure ineffective. This especially could occur in patients with severe rubeosis iridis.

An additional problem that could result with the known implant is that the patient could suffer from hypotony for a time period lasting from implantation until formation of the fibrous capsule around the implanted materials. Hypotony occurs when aqueous outflow from the chamber exceeds aqueous production as seen after insertion of the implant and causes too low an intraocular pressure and a corresponding flat anterior chamber. This could lead to further pathologic problems such as cataracts, adhesions of iris to cornea or lens, and in eyes which have had prior surgery, hemorrhagic choroidal detachments with a resultant loss of vision.

Further, although encapsulation of the implant is necessary for success of the surgical procedure, limiting the thickness of the capsule wall is desirable since this allows less restrictive movement of aqueous fluid out of the encircling band into the orbit and thereby ensures a good flow of aqueous. The known procedure did not possess this desired benefit.

Others have sought to remedy these problems, most notably the hypotony problem which occurs shortly after surgical implantation.

U.S. Pat. No. 3,788,327 to Donowitz et al disclose a surgical implant device. The Donowitz et al device is designed to rest on the surface of the cornea whereby a shank-like member with a valve to control intraocular pressure is mounted through the eye into the anterior chamber. Because the device is physically mounted onto the eye itself, friction occurs between the eyelid and the device. Additionally, the escaping aqueous flows to the cornea and not to the orbit. Furthermore, the valve in the Donowitz et al device must be permanently mounted in the shank to control the pressure in the anterior chamber.

U.S. Pat. No. 4,402,681 to Haas et al disclose an artificial implant valve. This valve is disadvantageous in that it is mounted into the posterior segment of the eye, and therefore it is difficult to adjust or remove the valve in the event of surgical complications. Further, the valve must remain permanently mounted to the eye to be effective. In addition, the construction of the valve in the Haas et al patent is composed of several parts and is complex.

Klupin et al disclosed valve implants for reducing intraocular pressure in an article entitled "Valve Implants in Filtering Surgery", *American Journal of Opthalmology*, Vol. 81, No. 2, pp. 232–235, 1976. The Krupin et al implant consists of a supramid tube which is cemented to a silastic tube. The end of the supramid tube is beveled and surgically inserted into the anterior chamber. The silastic tube remains outside the anterior chamber and has on its surface horizontal and vertical slits which function as a unidirectional valve. The Krupin et al device poses problems in that the valve is located in the silastic tube outside the anterior chamber. Therefore, if there are problems with the device, the conjunctiva and Tenon's Capsule must be surgically re-entered. Further, the device is designed so that the valve must be permanently mounted in the device if the device is to be effective.

Molteno et al also have developed a method of treating glaucoma. See Molteno et al, "Two Stage Insertion of Glaucoma Drainage Implants", *Trans. Ophthal. Soc. N.Z.*, Vol. 31, pp. 17–26, 1979. According to the Molteno et al technique, a silicone tube is attached to a circular plate which is sutured to the globe. A silastic tube which is connected to the plate is sutured to the sclera but is not inserted into the anterior chamber. Eight weeks later, a second operation is performed whereby the silastic tube is inserted into the anterior chamber. The Molteno et al procedure, therefore, requires two separate surgical operations to treat neovascular glaucoma and prevent hypotony.

White has disclosed a glaucoma pump shunt in "A New Implantable Ocular Pressure Relief Device: A Preliminary Report", *Glaucoma*, Vol. 7, pp. 289–294, 1985. The device consists of an inlet tube, an outlet tube, and a reservoir which connects the two tubes. Valves are located in both the inlet tube and the outlet tube, each valve located near the connecting reservoir. The end of the inlet tube located opposite from the connecting reservoir is mounted into the interior chamber. The reservoir is seated on the sclera and the posterior portion of the outlet tube is positioned in the sub-Tenon's space. This device is disadvantageous because of the intricate mounting of the reservoir and outlet tube, and because the inlet tube valve is located on the sclera and not in the anterior chamber, making it difficult to repair or replace the valve in case of failure. Additionally, because of the design of this system, the inlet and outlet valves are permanently mounted to the inlet and outlet tubes for the entire period when the device is implanted. Furthermore, the device is designed so that the reservoir permanently rests on the sclera and can potentially cause friction and erosion of the sclera and the conjunctiva.

Thus, a need exists for a simplified surgical procedure to treat glaucoma which may be performed in one step where the implanted device is easily accessible if follow-up surgery is needed to correct complications. Further, a need exists to prevent hypotony shortly after the surgical device is implanted. Additionally, a need exists to regulate the volume of aqueous flowing from the anterior chamber and to ensure that aqueous flows from the chamber to thereby prevent a buildup of intraocular pressure. Further, a need exists to prevent bleeding associated with the surgical technique and to prevent clogging of the implant caused by blood clots located in the opening or within the lumen of the tube of the implant.

SUMMARY OF THE INVENTION

A purpose of the present invention is to provide a one-step surgical procedure whereby an implant is constructed by suturing one end of a silastic tube to a silicone band whereby the other end of the silastic tube is mounted to be displaced away from the silicone band. The silicone band is positioned around the globe beneath the four rectus muscles of the eye. The displaced end of the silastic tube is then inserted via a needle tract into the anterior chamber under a scleral flap hinged at the limbus, defined by cauterizing the incision tract with a needle, inserting the needle into the anterior chamber and withdrawing it, injecting hyaluronic acid into the anterior chamber, and inserting the end of the silastic tube into the anterior chamber through a bead of hyaluronic acid. Further, a valve is located in the silastic tube at the end which is inserted into the anterior chamber so that upon insertion of the silastic tube into the anterior chamber, the pressure of aqueous flowing from the anterior chamber can be controlled to prevent hypotony. Flow of aqueous is restricted for a period of time, typically ten days to two weeks, and the valve may then be non-surgically destroyed or vaporized since hypotony is no longer a complication of the surgical procedure. The location of the valve is close to the front of the eye so that it may be eliminated by a laser. Additionally, the valve may be constructed of a biodegradable substance such as collagen which will break down after a desired period of time.

In an alternative embodiment of the invention, the silastic tube may be connected to a silicone tube which encircles the orbit. If this implant is used, clotting can occur in the larger silicone tube which would prevent the diffusion of aqueous from the anterior chamber into the orbit. To prevent the clotting, holes are drilled in the silicone tube so that diffusion may occur. The holes are of a critical size so that tissue bridges the holes rather than invading and thereby plugging the holes which would prevent escape of the aqueous.

When the silicone tube or silicone band is sutured to the sclera of the eye, the orbit forms an encircling capsule around the implant where it has been mounted. Although this is necessary for the effective diffusion of aqueous into the orbit, it would be desirable to limit the density of the capsule wall since this would allow less restrictive movement of aqueous fluid out of the encircling reservoir and into the orbit. Therefore, the silastic tube and silicone band or silicone tube are coated with a heparin complex prior to surgical insertion to obtain a much less dense fibrous capsule. In addition to limiting the density of the capsule wall, the heparin serves to prevent the formation of clots along the aqueous pathway in contact with the implant.

Accordingly, it is an object of the present invention to provide an implant and a surgical technique to treat neovascular and other refractory glaucomas by reducing intraocular pressure in the anterior chamber without causing the patient to be subjected to dangerous side effects.

A further object of the present invention is to provide an implant and a surgical technique for treating neovascular and other refractory glaucomas whereby a sufficient pressure is maintained in the anterior chamber at the time of surgery and shortly thereafter to prevent hypotony.

A further object of the present invention is to provide an implant and a surgical procedure for treating neovascular and other refractory glaucomas whereby bleeding and blood clotting are minimized during and shortly after surgery.

An additional object of the present invention is to provide an implant and a surgical technique for treating neovascular and other refractory glaucomas whereby flow of aqueous from the anterior chamber to the orbit is maintained and whereby the body forms a thin walled fibrous capsule around the surgical implant.

Other objects and features of the present invention will become apparent to those skilled in the art when reference is made in the following description taken in conjunction with the accompanying drawings.

DETAILED DESCRIPTION OF THE DRAWINGS

Figure 1:
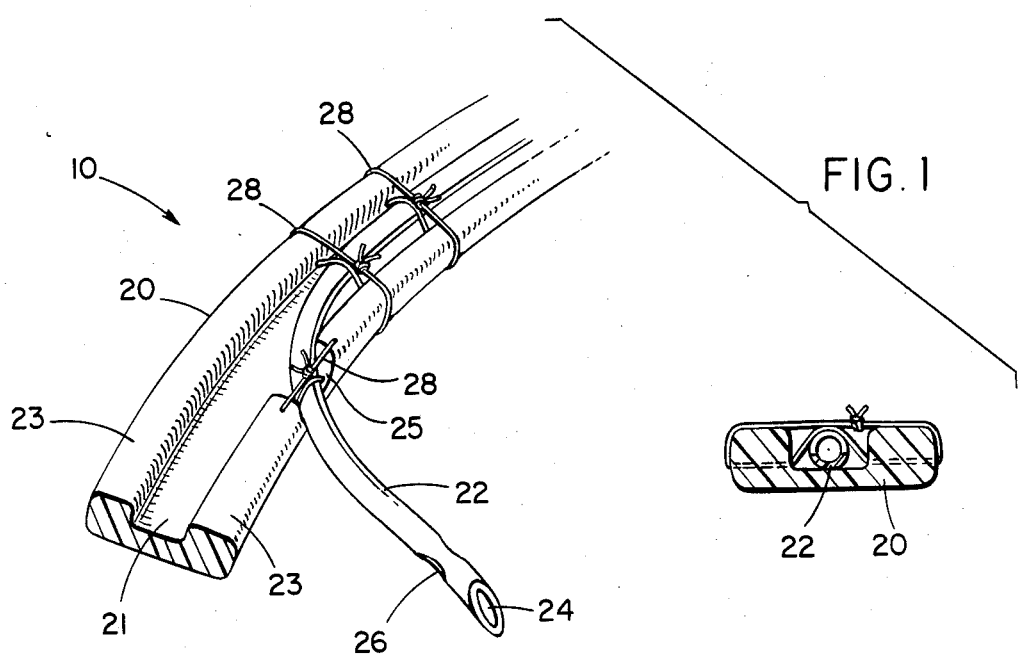
FIG. 1 is a view of a surgical implant which embodies the teachings of the instant invention.

In describing the invention illustrated in the drawings, specific terminology will be resorted to for the sake of clarity. However, the invention is not intended to be limited to the specific terms so selected, and it is to be understood that each specific term includes all technical equivalents which operate in a similar manner to accomplish a similar purpose.

Referring now to the drawings, and more particularly to FIG. 1, the basic elements of the inventive surgical implant are collectively designated as 10. Generally, implant 10 is constructed by mounting a silastic tube 22 to a silicone band 20. In the preferred embodiment of the present invention, silicone band 20 is a No. 20 type silicone band approximately 76 millimeters long and silastic tube 22 is 30 millimeters long, with an inside diameter of 0.30 millimeters and an outside diameter of 0.64 millimeters. In the preferred embodiment of the present invention, band 20 and tube 22 are both made of silicone polymers.

Silicone band 20 has a U-shaped groove 21 located at the center of one side of band 20. One end of tube 22 is placed in groove 21 and is fastened to band 20 by sutures 28 or by any suitable equivalent.

The U-shaped groove 21 in silicone band 20 is defined by raised parallel sides 23 joined together by a groove bottom member. If the end of tube 22 which is mounted in groove 21 of band 20 becomes misaligned with groove 21 and intersects either side 23 allowing the tube end to touch with the episclera instead, fibrous tissue could encapsulate the intersection of tube 22 with side 23, block the opening of tube 22, and decrease the effectiveness of the implant. Therefore, it is important that tube 22 be securely mounted in the center of groove 21 to prevent encapsulation and clogging of tube 22.

To further secure the tube terminus, ¾ of the inner wall of tube 22 is removed and the remaining tongue of silastic tube 22 is permanently secured to band 20 by a 5-0 Supramyd suture. The silicone band 20 inhibits fibrous ingrowth into silastic tube 22 only if tube remains in contact with band 20.

On one of raised sides 23 an indentation 25 is constructed by removing part of side 23. The end of tube 22 not secured in groove 21 is inserted in indentation 25 and is fastened to side 23 in indentation 25 by suture 28 or any other suitable fastening means.

The end of tube 22 which is mounted in indentation 25 of side 23 is obliquely cut to maximize the opening 24 of tube 22, which opening is designed to reside in the anterior chamber. Additionally, tube 22 contains a valve 26 located near opening 24 and mounted inside tube 22 by any suitable mechanism.

Before insertion of implant 10 into the eye, a 360° peritomy is made posterior and parallel to the limbus at the junction of cornea and sclera, except superiorly where the conjunctival incision is extended posteriorally. In the preferred embodiment of the surgical technique, the peritomy is made 4 to 5 millimeters posterior to the limbus and the conjunctival incision is extended posteriorally for 8 millimeters. A vitreous tap is performed if, despite pharmaceutical treatment, the intraocular pressure is equal to or greater than 40 millimeters of mercury. Traction sutures are then placed under the four rectus muscles.

Figure 2:
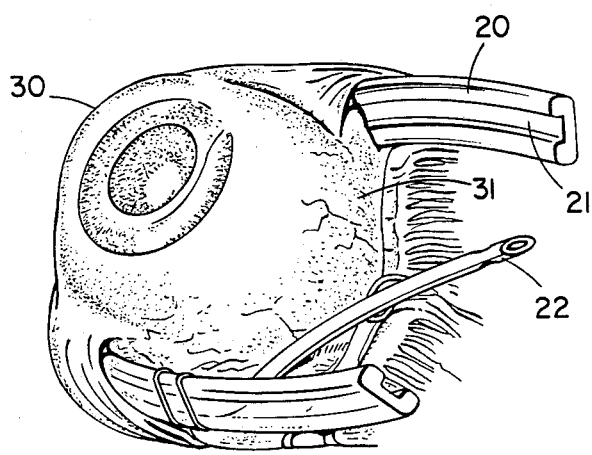
FIG. 2 is a view of the surgical implant where the silicone band is positioned around the globe and where the silastic tube is located anteriorally just temporal to the superior rectus muscle.
Figure 4:
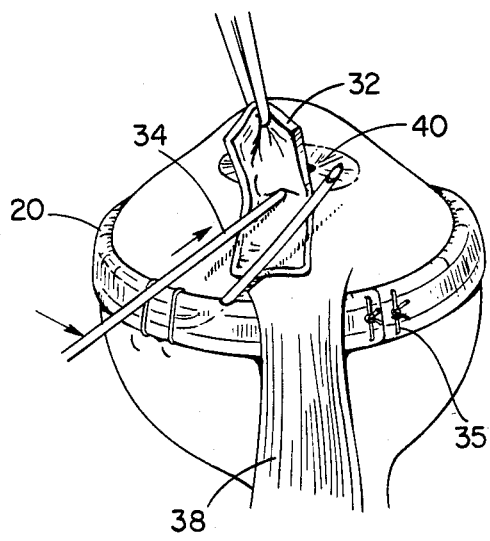
FIG. 4 is a view of an eye being treated with a cauterized needle before insertion of the silastic tube into the anterior chamber.
Figure 5:
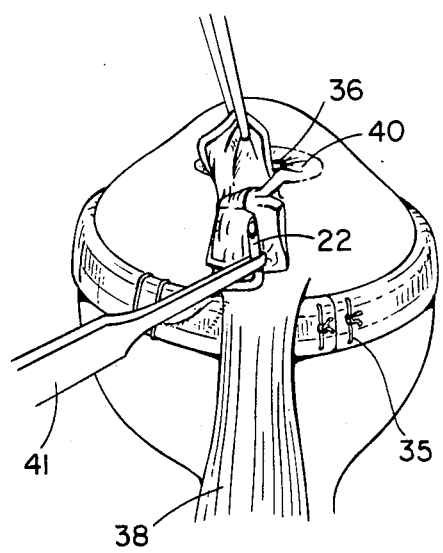
FIG. 5 is a view of the silastic tube being inserted into the anterior chamber.

Referring to FIGS. 2, 4, and 5, band 20 is positioned around the maximum circumference of the eye 30 (i.e. the equator), beneath the four rectus muscles 38, with groove 21 facing sclera 31. Band 20 is fastened to sclera 31 by fasteners such as sutures 35 (See FIGS. 4, 5) in the four quandrants such that the anterior edge of band 20 is located just posterior to the insertion of the rectus muscles. In the preferred surgical technique, the anterior edge is located approximately 10 to 12 millimeters from the limbus. The end of silastic tube 22 which is extended from band 20 should emerge from band 20 anteriorly, just temporal to the superior rectus. (See FIGS. 2, 4).

Figure 3:
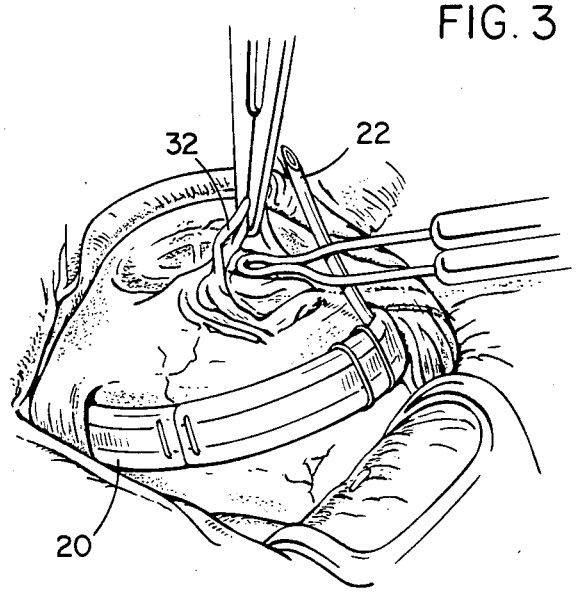
FIG. 3 is a view of an eye before the surgical implant is inserted into the anterior chamber.

Referring to FIG. 3, a limbal based scleral flap 32 is raised and carried forward into the clear cornea. According to the preferred surgical technique, the flap measures 4 millimeters by 4 millimeters and is carried forward one millimeter into the clear cornea. Tube 22 is then anchored to the posterior and temporal edges of the scleral bed so that, on insertion, tube 22 lies over the nasal iris. In the preferred surgical technique utilized when practicing the invention, anchoring is accomplished by 10-0 nylon sutures.

Entry to anterior chamber 40 is effected first by directing a needle 34 into anterior chamber 40 (See FIG. 4). In the preferred surgical technique, the needle is 25-gauge (0.5 mm outside diameter) and is bent to allow entry parallel to the iris. To prevent bleeding caused by entry of the needle 34 into a highly neovascularized angle, needle 34 is touched with a wet-field cautery to obtain coagulation of the ruptured bleeding angle vessels upon insertion. On withdrawal of needle 34, anterior chamber 40 becomes shallow due to loss of aqueous. Hyaluronic acid (Healon ®) is injected into anterior chamber 40 through a 23-gauge needle (0.65 mm outside diameter) to restore anterior chamber 40 with hyaluronic acid. In the preferred surgical technique, 0.1 to 0.3 milliliters of hyaluronic acid is injected to deepen the chamber to full depth. The needle is removed from the anterior chamber 40 and the hyaluronic acid refluxes to form a bead 36 which indicates the opening to the anterior chamber 40 (see FIG. 5).

Figure 6:
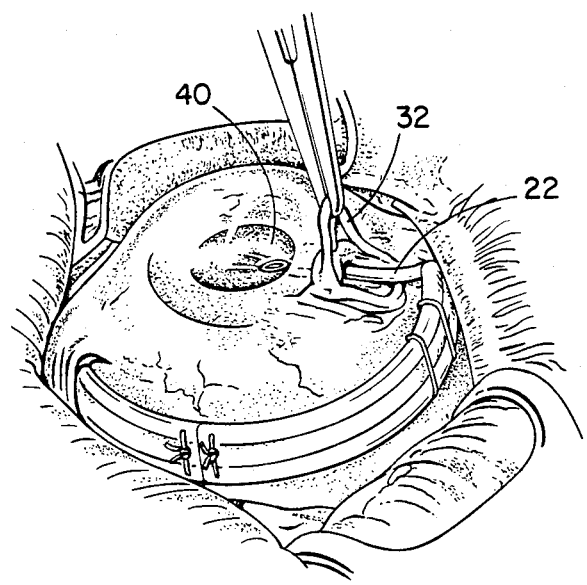
FIG. 6 is a view of an eye after the silastic tube is inserted into the anterior chamber.

The end of tube 22 lying over the nasal iris is compressed between the jaws of a microforceps 41 (see FIG. 5), and is introduced into anterior chamber 40 by insertion through bead 36. Tube 22 is inserted into anterior chamber 40 until the desired length of tube 22 has entered the chamber (See FIG. 6). According to the preferred surgical technique utilized when practicing the present invention, the tube should extend approximately 3 millimeters into the anterior chamber.

Figure 7:
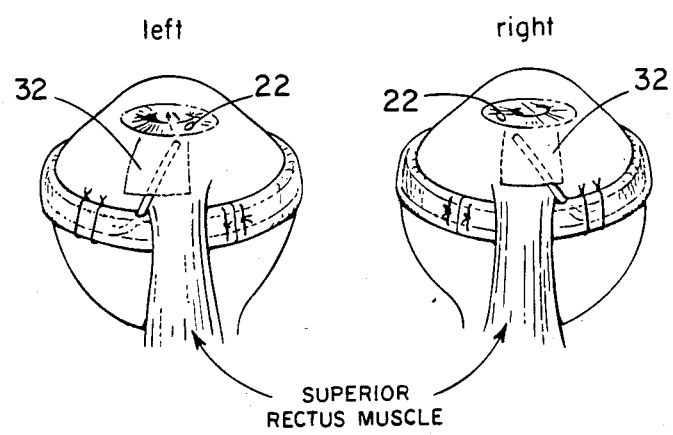
FIG. 7 is a view of the left eye and the right eye after completion of the inventive surgical procedure.

Scleral flap 32 is then closed by suitable means such as nylon sutures located at the two posterior corners. (See FIG. 7). Scleral flap 32 is made slightly temporal to the mid-line in each eye to allow coverage of silastic tube 22, which is angled towards the nasal iris. Tenon's capsule over the tube is closed separately from the conjunctiva by suitable means such as a running 7-Vicryl suture. The conjunctiva is then closed by a suitable means such as a continuous 6-0 plain cat gut suture. 40 mg of Gentamicin sulfate and 4 mg of dexamethasone phosphate are injected into the inferior subconjunctival space to complete the surgical technique.

This procedure results in the formation of a fibrous capsule surrounding silicone band 20. The capsule forms within ten days to two weeks after implantation and is apparently an attempt of the body to destroy or isolate what the host tissue recognizes to be a foreign substance, namely, silicone band 20. Aqueous fluid draining from anterior chamber 40 through tube 22 into band 20 is known to diffuse into and expand this capsule. Fibrous encapsulation of silicone band 20 is essential for the success of the surgical procedure because the capsule acts as the wall of the reservoir through which aqueous diffuses into the orbit to be picked up by orbital vessels which return the fluid to the general blood circulation.

Valve 26 of tube 22 is located in the anterior chamber when implant 10 is in place. Valve 26 in this embodiment, takes the form of a restriction and is provided in tube 22 to limit flow of aqueous out of anterior chamber 40 immediately after the surgical implant; this prevents anterior chamber 40 from flattening due to hypotony. The risk of hypotony after the surgery described above has been shown to exist until such time that fibrous encapsulation occurs. By utilizing valve 26 during this critical period, outflow of aqueous by the ciliary body from anterior chamber 40 is restricted to approximate aqueous production so that anterior chamber 40 maintains intraocular pressure at a safe level.

Because valve 26 need only be temporary, tube 22 is positioned in anterior chamber 40 so that this embodiment of valve 26 resides in anterior chamber 40; in this manner, valve 26 may be destroyed or vaporized by surgical laser procedures without requiring the removal of tube 22 from anterior chamber 40 after the critical 10 day to two week time period.

In another embodiment, valve 26 is made from a biodegradable material such as collagen, so that after the desired period of time, here ten days to two weeks, the valve self-destructs. The use of other equivalent valves is contemplated by the present invention, just so long as the valve restricts fluid flow during the critical period and subsequently is disabled or itself becomes disabled. It is preferable, however, to position valve 26 where it readily is visible, as by locating it in anterior chamber 40, so that if intraocular pressure increases in the eye, the valve readily can be inspected to determine if the cause of the problem is the valve.

To limit the density of the fibrous capsule walls (i.e., to maximize fluid flow and prevent clotting), a more bioreactive silicone implant may be inserted. One such method of creating a more bioreactive silicone implant is to fix a heparin complex to the silicone polymer.

Heparin, a substance normally found in ocular tissues, is an acid mucopolysaccharide or glycosaminoglycan, and is therefore a more bioreactive material than a silicone polymer. The heparin fixing process consists of immersing implant 10 in a solution of heparin-quaternary ammonium compound-complex in an organic solvent, removing the organic solvent, and sterilizing by gas or heat. The amount of complex fixed to the surface is approximately 40 μg/cm²; the surface concentration is controlled by the concentration of the complex and the duration of the immersion.

The complex between heparin and tridodecylmethylammonium chloride (TDMAC) is formed when heparin, an acid mucopolysaccharide with an overall negative charge, is exposed to the TDMAC ammonium ion which is positively charged.

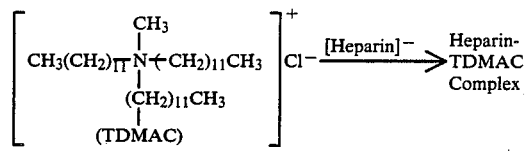

To effectively coat tube 22 and band 20 with a heparin solution, all surfaces of tube 22 and band 20 are treated with a one percent solution of the Heparin-TDMAC complex in 1:1 toluene/petroleum ether at room temperature for 30–60 seconds. Tube 22 and band 20 are then flushed with compressed air, and dried overnight in a vacuum oven to remove traces of the volatile organic solvent.

During the immersion process, the surface of the silicone polymer is swollen by the organic solvent, allowing penetration of the polymer surface by the hydrophobic hydrocarbon chains of the TDMAC portion of the complex. Removal of the organic solvent by evaporation results in firm fixation of the complex to the polymer surface as the polymer shrinks back to normal size. The surface-bound complex on polymers such as the present silicone implant is resistant to elution by saline or blood. Surface-bound heparin apparently causes thromboresistance in the same way as heparin does in solution. The presence of a heparin complex on the surface of silicone polymers probably simulates the naturally occurring heparin coat of the endothelium, thereby decreasing protein, leukocyte and platelet adherence, and resulting in prolonged coagulation time.

The heparin coating of tube 22 and band 20 effectively reduces the thickness of the fibrous capsule because the coating prevents the host tissue from fully recognizing the implant as a foreign body, and thus allows aqueous to flow through tube 22 into band 20 and diffuse through band 20 to the encapsulating fibrous tissue more rapidly.

Further, the heparin coating of silastic tube 22, acts to prevent tube obstruction by blood clots. A low intraocular pressure of 10 mm Hg is capable of flushing blood from heparinized tube 22 in 1 to 2 seconds whereas in a non-heparinized tube the intraocular pressure must be 60 mm Hg to flush the tube. If blood remains in the non-heparinized tube for 30 minutes, a pressure of 60 mm Hg is incapable of flushing the tube whereas in heparinized tube 22 the clot is expelled after 2 seconds.

Figure 8:
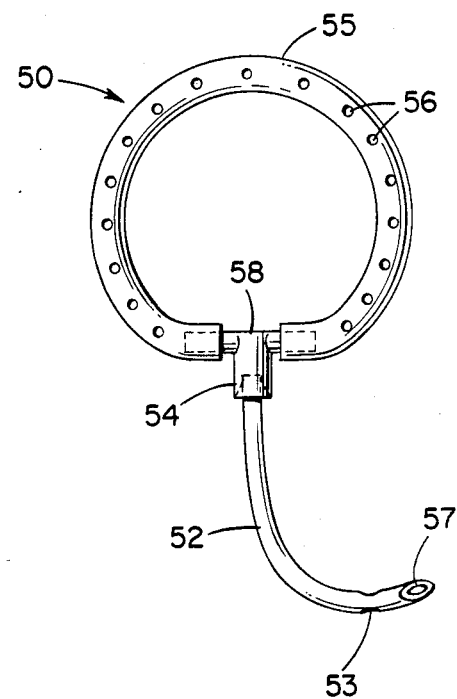
FIG. 8 is a view of an alternative embodiment of the surgical implant.

Referring to FIG. 8, the basic elements of an alternative embodiment of an implant embodying the teachings of the present invention are collectively designated as 50. One end of silastic tube 52 is connected to a larger silastic tube 55 by means of a T-connector 58. In the preferred embodiment of the invention, the length of tube 52 is 40 millimeters with an inside diameter of 0.30 millimeters and an outside diameter of 0.62 millimeters. Tube 55 is approximately 75 millimeters long and has an inside diameter of 2 millimeters. The end of tube 52 not connected to tube 55 has an oblique opening 57 and valve 53 mounted on the inside, near opening 57.

Implant 50 is then treated with a heparin complex as described above to prevent blood clotting and obstruction of the lumen of tubes 52 and 55, and T-connector 58 and one end of tube 55 is secured to the sclera by suitable means such as Supramid sutures prior to the raising of a limbal scleral flap. One end of tube 55 is connected to T-connector 58. The other end of tube 55 is passed beneath the four rectus muscles and is secured to the sclera in the four quadrants at the equator by suitable means such as 4-0 Supramid sutures and is connected to T-connector 58 to form a circular passageway which surrounds the orbit.

Silastic tube 52 is inserted into the anterior chamber and is connected to tube 55 as follows. A malleable steel wire, not pictured, is inserted into the interior of tube 52 so that an appropriate curve of entry is obtained into the anterior chamber. Tube 52 and the wire is then inserted into the anterior chamber, the wire is removed, and the end of tube 52 not located in the anterior chamber is secured to T-connector 58 by any suitable means such as silicone glue 54. The assembly of tube 52, tube 55 and T-connector 58 allows aqueous from the anterior chamber to flow in both directions upon leaving tube 52, and thereby obtains full utilization of encircling tube 55.

As in implant 10, implant 50 contains valve 53 so that the fall in intraocular pressure in the anterior chamber is not excessive upon insertion of implant 50. Valve 53, like valve 26 of implant 10, is located in tube 52 near end 57 so that it readily can be seen when tube 52 is inserted into the anterior chamber. Valve 53 may be destroyed or vaporized by laser surgery as described for valve 26, or may be made from a biodegradable material, such as collagen.

Holes 56 are created in the wall of tube 55 beyond the region where tube 52 is located to provide for diffusion of aqueous from the anterior chamber. The holes are created, for example, by using an argon blue laser at a setting of 3 watts for two seconds duration. In the preferred embodiment, approximately fifteen holes with a diameter of 50 microns (50 $\mu$m) are created in the wall of tube 55. The size of holes 56 are critical. If holes having a diameter significantly greater than 50 microns (50 $\mu$m) are created in the wall of tube 55, fibrous tissue will tend to invade holes causing them to clog and therefore prevent the diffusion of aqueous through tube 55. Therefore, the diameter of holes 56 must be smaller than 50 microns to allow adequate diffusion of aqueous from the anterior chamber. In the preferred embodiment of the invention, 50 micron holes were selected because this is the smallest diameter hole that can be made by using commercial lasers. However, the size of the holes selected could be any diameter up to 50 microns.

From the above, it should be apparent that many modifications and variations of the present invention are possible. It is therefore to be understood that, within the scope of the appended claims, the invention may be practiced otherwise than as specifically described.

What is claimed is:

1. An implant for use in a surgical technique to treat neovascular or refractory glaucomas, said implant comprising:
   a tube sized so that one end thereof may be inserted into the anterior chamber of the eye,
   a band sized so as to fit around the equator of the eye, said band containing a U-shaped groove sized to surround said tube,
   one end of said tube being mounted in said groove, and the other end of said tube having an oblique opening and said other end further containing a physically destructible initial temporary restriction located therein the region of said opening.
2. The implant according to claim 1, wherein said tube and said band are both made of silicone polymers.
3. The implant according to claim 1, wherein said implant has a heparin complex fixed to all surfaces of said tube and to all surfaces of said band.
4. The implant according to claim 1, wherein said restriction is made of collagen.
5. An implant for use in a surgical technique to treat neovascular or refractory glaucomas, said implant comprising:
   a first tube sized so that one end thereof may be inserted into the anterior chamber of the eye, and
   a second tube, larger than said first tube, sized so as to fit around the equator of the eye,
   one end of said first tube being connected to said second tube, the other end of said first tube having an opening therein and containing a physically destructive initial temporary restriction in the region of said opening, said second tube being provided with holes throughout the wall thereof sized so that aqueous can diffuse from the anterior chamber through said holes and sized so that said holes are not invaded with fibrous tissues.
6. The implant according to claim 5, wherein both tubes are made of silicone polymers.
7. The implant according to claim 5, wherein said implant has a heparin complex fixed to all surfaces of both tubes.
8. The implant according to claim 5, wherein said restriction is made of collagen.
9. The implant according to claim 5, wherein said holes are 50 microns in diameter or less.
10. A method for treating neovascular or refractory glaucomas with a surgical implant, said method comprising the steps of:
    securing one end of a tube which is sized so that it is adapted to fit into the anterior chamber of the eye in a U-shaped groove of a band sized so as to fit around the equator of the eye,
    mounting the band around the equator of the eye,
    inserting the other end of said tube into the anterior chamber of the eye,
    temporarily restricting the flow of aqueous from the anterior chamber into the tube,
    subsequently removing the restriction to the flow of aqueous from the anterior chamber into said tube,
    said aqueous flowing through said tube, into said band, and then from said band into the orbit.
11. A method according to claim 10, which includes the step of treating said tube and said band in a heparin solution prior to mounting said band around the equator of the eye.
12. A method for treating neovascular glaucoma with a surgical implant, said method comprising the steps of:
    connecting one end of a first tube, sized so that one end is adapted to fit into the anterior chamber of the eye, to a second and larger tube, sized so as to fit around the equator of the eye, said second tube being provided with holes therethrough,
    inserting the other end of said first tube into the anterior chamber of the eye,
    temporarily restricting the flow of aqueous from the anterior chamber into said first tube,
    subsequently removing the restriction to the flow of aqueous from the anterior chamber into said first tube, and then into said larger tube,
    said aqueous flowing through said first tube, into said second tube, and then diffusing through said holes into the orbit.
13. A method according to claim 12, which includes the step of treating the first tube and the second tube in a heparin solution prior to mounting the second tube around the equator.

* * * * *